Figure 1A:
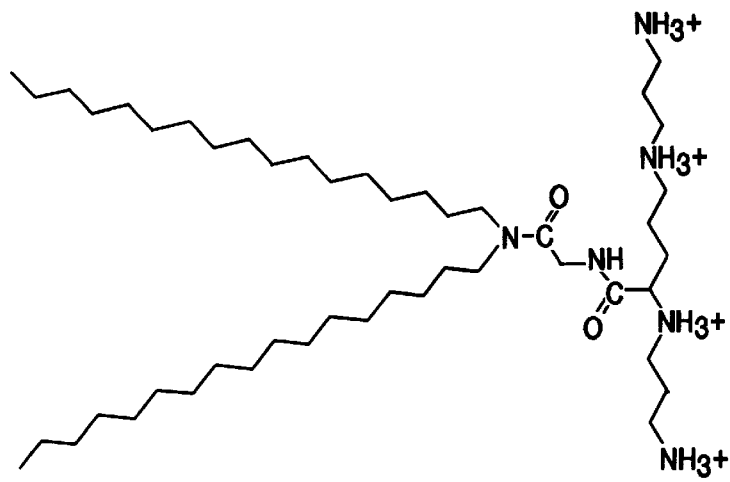

United States Patent [19]
Vacus et al.

[11] Patent Number: 6,156,338
[45] Date of Patent: Dec. 5, 2000

[54] METHOD FOR PREPARING COMPOSITIONS FOR TRANSFERRING NUCLEIC ACIDS

[75] Inventors: Joël Vacus, Paris; Tsiala Bouknikachvili, Sainte Genevieve Des Bois, both of France

[73] Assignee: Aventis Pharma S.A., Antony Cedex, France

[21] Appl. No.: 09/269,515

[22] PCT Filed: Oct. 3, 1997

[86] PCT No.: PCT/FR97/01747

§ 371 Date: Apr. 2, 1999

§ 102(e) Date: Apr. 2, 1999

[87] PCT Pub. No.: WO98/15639

PCT Pub. Date: Apr. 16, 1998

[30] Foreign Application Priority Data

Oct. 8, 1996 [FR] France .................................. 96 12259

[51] Int. Cl.[7] .................................................. A61K 9/127
[52] U.S. Cl. ...................... 424/450; 435/458; 435/320.1; 536/23.1
[58] Field of Search ........................... 435/6, 320.1, 458; 424/450; 514/44; 536/23.1

[56] References Cited

U.S. PATENT DOCUMENTS 4,873,089 10/1989 Scotto et al. .
5,846,947 12/1998 Behr et al. .

FOREIGN PATENT DOCUMENTS

WO 89/05636  6/1989  WIPO .
WO 95/18863  7/1995  WIPO .
WO 96/17823  6/1996  WIPO .

OTHER PUBLICATIONS

Behr et al., Efficient Gene Transfer into Mammalian Primary Endocrine Cells with Lipopolyamine–Coated DNA., Proc. Natl. Acad. Sci. USA 86: 6982–6986 (1989).

Bringham et al., Expression of a Procaryotic Gene in Cultured Lung Endothelial Cells after Lipofection with a Plasmid Vector, Am. J. Respir. Cell Mol. Biol. 1:95–100 (1989).

Demeneix et al., Gene Tranfer into Intact Vertebrate Embryos, Int. J. Dev. Biol. 35: 481–484 (1991).

Duzgunes et al., Fusion of Liposomes Containing a Novel Cationic Lipid, N–[2, 3–(Dioleyloxy)propyl]–N,N,N–trimethylammonium: Induction by Multivalent Anions and Asymmetric Fusion with Acidic Phospholipid Vesicles., Biochemistry, 28: 9179–9184 (1989).

Fasbender et al., Optimization of Cationic Lipid–Mediated Gene Tranfer to Airway Epithelia, Am. J. Physiol. 269; 45–51 (1995).

Felgner et al., Lipofection: A Highly Efficient Lipid–Mediated DNA–Transfection Procedure, Proc. Natl. Acad. Sci. USA 84: 7413–7417 (1987).

Gao et al., A Novel Cationic Liposome Reagent for Efficient Transfection of Mammalian Cells, Biochem. Biophys. Res. Com. 179: 280–285 (1991).

Gershon et al., Mode of Formation and Structural Features of DNA–Cationic Liposome Complexes Used for Transfection, Biochemistry 32: 7143–7151 (1993).

Gustafsson et al., Complexes between Cationic Liposomes and DNA Visualized by Cryo–TEM, Biochim. Biophys. Acta 1235: 305–312 (1995).

Hui et al., The role of Helper Lipid Cationic Liposome–Mediated Gene Transfer, Biophys. J. 71: 590–599 (1996).

Hofland et al., Formation of Stable Cationic Lipid/DNA Complexes for Gene Transfer, Proc. Natl. Acad. SCI. USA 93: 7305–7309 (1996).

Pinnaduwage et al., Use of a Quaternary Ammonium Detergent in Liposome Mediated DNA Transfection of Mouse L–Cells, Biochim. Biophys. Acta 985: 33–37 (1989).

Sternberg et al., New Structures in Complex Formation between DNA and Cationic Liposomes Visualized by Freeze–Fracture Electron Microscopy. , FEBS Lett. 356: 361–366 (1994).

Xu et al., Mechanism of DNA Release from Cationic Liposome/DNA Complexes Used in Cell Transfection, Biochemisry 35: 5616–5623 (1996).

Noevir, Preparation of liposome —by heating liposome componenet membrane to not lower than phase transition temperature with small amount of aqueous solution, cooling, etc., Database WPI, Section Ch, Week 8851, Derwent Publications (1988).

Xiaohuai Zhou et al, Improved Encapsulation of DNA in pH–Sensitive Liposomes for Transfection, Journal of Liposome Research, vol. 2, No. 1, pp. 125–139 (Jan. 1, 1992).

Barthel, F. et al., Gene Transfer Optimization with Lipospermine–Coated DNA, DNA and Cell Biology, vol. 12, No. 6, pp. 553–560 (Jul. 1, 1993).

Chun–Jung Chu et al, pH–Sensitive Liposomes, Journal of Liposome Research, vol. 4, No. 1, pp. 361–395 (Mar. 1, 1994).

*Primary Examiner*—James Ketter

[57] ABSTRACT

The invention concerns a method for preparing a composition for transferring nucleic acids consisting in contacting a nucleic acid with a cationic lipid, whereby, previous to contacting, the cationic lipid is subjected to a heating step. The invention also concerns the resulting compositions and their use.

26 Claims, 15 Drawing Sheets

METHOD FOR PREPARING COMPOSITIONS FOR TRANSFERRING NUCLEIC ACIDS

The present invention relates to a process for the preparation of compositions for the transfer of nucleic acids. The compositions obtained can be used for the transfer of nucleic acids into cells in vitro, ex vivo or in vivo.

The cellular penetration of a naked nucleic acid (generally of high molecular mass and negatively charged) is a rare phenomenon which, in general, only leads to the transfection of the cell with a very limited efficiency. For this reason, various types of vectors and techniques have been described in the prior art for carrying out this transfer. Two large families can be distinguished in this regard: viral vectors and physical techniques.

Among the viral vectors, there may be mentioned, for example, retroviruses, adenoviruses, AAVs, herpesviruses, baculoviruses and the like. The transfer efficiency obtained with viral vectors is generally very good. However, their construction and their production are difficult, the cloning capacity of these vectors is sometimes limited, and their use may, in some cases, exhibit certain disadvantages inherent in the use of viruses (spreading, pathogenicity and the like).

For these reasons, various physical techniques for the transfer of nucleic acids have been developed. There may be mentioned, for example, electroporation, coprecipitation or the use of particle guns.

Electroporation consists in applying an electric field to a cell suspension containing DNA. However, while this technique gives good results in some cases, it is difficult to optimize because of the risk of irreversible lesions of the cell membrane. In the particle gun technique, particles (gold, tungsten) are coated with nucleic acids and then discharged onto the cells. This method is however promising mainly for cells with a wall, such as plant cells. Moreover, the coprecipitation of DNA with certain polymers (DEAE-dextran) or calcium phosphate has the disadvantage of not being very reproducible and of being sometimes cytotoxic.

To overcome these disadvantages, synthetic transfer vectors have been developed. The role of these vectors is essentially to provide the nucleic acid in a form appropriate for cell penetration, to facilitate this penetration (into the cytoplasm and then into the nucleus) as well as to protect it from cytoplasmic nucleases.

Among these vectors, the cationic lipids possess advantageous properties. These vectors consist of a polar cationic part allowing the condensation of the nucleic acids and of a hydrophobic lipid part stabilizing the ionic interaction. An excess of lipid, because of the ionization of its polar part, would also promote the interaction with the cell membrane. Specific examples of cationic lipids are in particular lipopolylysine, monocationic lipids (DOTMA; Lipofectin®); certain cationic detergents (DDAB); lipospermines (DOGS, DPPES, and the like), lipothermines, and the like.

The use of this type of vector, optionally in combination with a fusogenic lipid (DOPE and the like), has shown that they possess good nucleic acid transfer properties in vitro, ex vivo and in vivo on numerous cell types. These vectors therefore constitute an advantageous alternative to the viral vectors and to the physical techniques for the transfer of nucleic acids. However, the exploitation of these vectors at the industrial level is currently limited. In particular, the methods of preparing these vectors which are described in the prior art are empirical, not very industrializable, not very reproducible and lead to poorly defined mixtures whose composition does not give optimum properties.

Accordingly, it is known to prepare compositions by mixing various lipid components in chloroform, drying in a stream of nitrogen for 20 minutes and then drying under vacuum. The lipid film thus obtained is taken up in deionized water [Hui 96], [Felgner 87]. The mixture is then vortexed in order to resuspend the lipid and sonicated in a sonication bath for 10 minutes until clarification of the suspension which can then be diluted. Compaction is immediately performed before addition over the cells and left for 4 hours at 37° C. in an F10 culture medium. Variants of this technique exist. For example, after dissolution with chloroform and drying, the film can be taken up in a 20 mM NaCl solution [Guershon 93] or 20 mM Hepes buffer [Gao 91]. The suspension is generally vortexed (immediately after taking up the film or after a hydration phase of 24 hours at 4° C. [Gao 91]) and sonicated for varying amounts of time. Sometimes, the ionic strength and the nature of the ions of the complex can be modified after compaction [Xu 1996]. The sonication operation itself comprises variants since some authors use sonication probes made from titanium [Gustafsson 1995].

The procedure consisting of the formation of a film by dissolution with chloroform, evaporation, drying, taking up in an aqueous medium and sonication is also frequently encountered for the manufacture of liposomes composed of a neutral lipid combined with a cationic surfactant [Pinnaduwage 89].

Another mode of preparation consists in directly diluting commercially available lipids (in an ethanolic solution, an aqueous suspension or a liposomal formulation) in an MEM culture medium. After an identical dilution of the DNA, the two components are mixed by inverting and the suspension is left at room temperature for 15 to 30 minutes. Another dilution is then performed before bringing into contact with the cells for 6 hours [Fasbender 95]. The commercially available lipid and the DNA can also simply be diluted separately in distilled water before bringing into contact simply by stirring and optionally incubating at room temperature for 15 minutes [Bringham 89].

According to other methods, the initial form of the lipid is an ethanolic solution of variable concentration which is freshly diluted in culture medium just before bringing into contact with the DNA [Behr 89]. The ethanolic solution can also be diluted in other media (water, NaCl at various concentrations) immediately or 10 minutes before compaction. After the compaction and optionally waiting for 10 minutes, another dilution may be made in a medium of variable ionic composition. The transfection is carried out after a period of 0 or 10 minutes after the last dilution [Barthel 93]. The ethanolic solution can also be introduced directly into the aqueous suspension containing the DNA and the mixture can be subsequently subjected to sonication in a bath [Demeneix 91].

It is also known to solubilize cationic liposomes composed of a DOSPA/DOPE mixture [Hofland 96] with a 1% solution of octylglucoside (OG) in a 10 mM solution of Tris (pH 7.4). After contacting with the DNA, the complex is dialysed three times (in order to remove the excess OG micelles) against 2000 volumes of 10 mM Tris/5% dextrose (pH 7.4) for more than 48 hours at a temperature of 4° C. The transfection is carried out for 4 to 5 hours at 37° C. in serum-free DMEM.

The preparation of the cationic liposomes can also be carried out by rehydration of the lipid film followed by successive extrusions through polycarbonate membranes of calibrated porosity [Düzgünes 89] or by microfluidization [Sternberg 94].

All these modes of preparation have disadvantages for extrapolation to an industrial scale. Sonication can hardly be used on such a scale and the stability of the vesicles thus formed often proves to be inadequate. Furthermore, the probes used for the sonication, of metallic origin, can liberate into the medium particles which are awkward for pharmaceutical applications. Likewise, filtration gives only liposomes whose size is defined by the porosity of the membrane after the filtration and whose stability over time is not assured. The use of lipids in the form of an ethanolic solution, besides the problem of using an organic solvent, is found to induce the formation of highly polydisperse particles.

The applicant has now developed a new process for the preparation of transfectant compositions.

This process stems more particularly from the characterization, by the applicant, of the physicochemical properties of lipid vectors. The applicant has thus shown that, depending on the conditions, these vectors exist in various physicochemical states (micellar form, mature aggregate form and the like). The applicant has made it possible more particularly to characterize the various physicochemical states of the lipid vectors; it has also demonstrated means which make it possible to control the passage between these various states, and to stop the maturation in defined states, which are appropriate for forming the complex with the DNA and for cell transfection. The present invention thus describes a reproducible process allowing the preparation, at the industrial level, of characterized and calibrated transfectant compositions.

The process of the invention is based more particularly on the carrying out of a preliminary treatment of the cationic lipid, allowing a homogeneous micellar suspension to be obtained. Thus, a first subject of the invention relates to a process for preparing a composition for the transfer of nucleic acids comprising bringing a nucleic acid into contact with a cationic lipid, characterized in that, prior to the bringing into contact, the cationic lipid is subjected to a heating step.

The applicant has studied the physicochemical characteristics of the various cationic lipids. The results obtained show that, depending on the ionic strength of the medium, depending on the pH of the medium or alternatively depending on the temperature, the cationic lipids exist in different physical states. The examples presented below describe in particular phase diagrams for different cationic lipids (lipospermines, lipothermines) as well as a study of the optical density as a function of the pH and of the temperature, which show clearly different physicochemical states depending on the conditions. The applicant has now shown that these different states had different properties of compaction with DNA and of cell transfection, and that it was advantageous to have a method which makes it possible to reproducibly control access to these different states.

The process according to the invention, which involves in particular the heating of the lipid suspension, has the advantage of a method which is simple and which can be easily applied to the constraints of industrial processing. It makes it possible, in addition, by controlling the kinetics of organization, to regulate the structure adopted by the lipid before and after bringing it into contact with the DNA. The process of the invention allows, in addition, standardization of the method of preparation, which is essential on the industrial scale.

More particularly, the preliminary step consists in heating the cationic lipid until a micellar solution is formed. Still more preferably, the lipid vector is heated to a temperature greater than its phase transition temperature. The phase transition temperature corresponds to the temperature at which the lipid chains melt. This temperature can be determined, for each lipid vector, by techniques known to persons skilled in the art. In particular, it is possible to use the Differential Scanning Calorimetry method (or DSC) by means, for example, of the DSC4 apparatus (Perkin Elmer), following the manufacturer's recommendations, as illustrated in the examples.

The process of the invention is applicable to any type of cationic lipid. It is particularly appropriate for the preparation of lipopolyamines. Lipopolyamines are amphiphilic molecules comprising at least one hydrophilic polyamine region and one lipophilic region covalently linked to each other by a chemical arm. Advantageously, the polyamine region corresponds to the general formula $H_2N-(-(CH)_m-NH-)_1-H$ in which m is an integer greater than or equal to 2 and 1 is an integer greater than or equal to 1, it being possible for m to vary between the different carbon groups which are between two amines. Preferably, m is between 2 and 6 inclusive and 1 is between 1 and 5 inclusive. Still more preferably, the polyamine region is represented by spermine or by thermine, or by an analogue which has conserved its properties of binding to DNA.

The lipophilic region may be one or more saturated or unsaturated hydrocarbon chains, cholesterol, a natural lipid or a synthetic lipid capable of forming lamellar or hexagonal phases. Advantageously, the lipophilic region comprises two hydrocarbon chains.

In addition, the cationic lipid may be combined with lipid adjuvants, as indicated further on.

Preferred examples of cationic lipids are in particular the lipospermines, in particular dioctadecylamidoglycyl spermine (DOGS) or palmitoylphosphatidylethanolamine 5-carboxyspermylamide (DPPES), whose preparation is described, for example, in patent application EP 394 111. Another preferred family consists of the lipothermines, among which there may be mentioned more particularly RPR120531 and RPR120535 (FR95/13490, WO96/17823 incorporated into the present by reference). The structure of these compounds is represented in FIG. 1.

To carry out the process of the invention, the lipid, in the form of a crystalline powder or a film, is taken up in pure water or a saline medium whose pH is optionally adjusted. The homogenization is achieved by heating above the transition temperature of the lipid, that is to say the temperature above which the aliphatic chains melt. As indicated above, this phase transition temperature can be determined by differential scanning calorimetry. In the case of DOGS for example, it is 38° C. in water at pH 7.5, and it is 44° C. at a pH of 8.8. No transition is observed in pure water at acidic pH; the lipid is in micellar form regardless of the temperature. The phase transition temperature also depends on the ionic strength of the medium. By way of example, the temperature of DOGS in a solution of NaCl is 44.4° C. at acidic pH, 42° C. at pH 7.5 and 39.8° C. at pH 9.9. This transition temperature is of course variable from one lipid to another (cf examples). In particular, for RPR120531, the phase transition temperature as determined by DSC and turbidimetry is 51.5° C. (powder) and 30° C. (hydrate, pH 7.5). For RPR120535, it is about 43° C. (hydrate, pH 7.5). The heating can be obtained on a waterbath, by direct heating, or alternatively by any means which makes it possible to raise the temperature. It allows the formation of a micellar solution characterized by the clarification of the suspension, if the pH conditions allow it. The presence of micelles was demonstrated by techniques such as turbidimetry, low-angle X-ray diffusion/diffraction and by transmission electron cryomicroscopy.

Another unexpected advantage of the process of the invention consists in the transfection efficiency of the compositions. Thus, in a particularly advantageous manner, the compositions obtained allow the transfection of cells independently of the presence of serum. It is indeed known that serum (foetal calf serum for example) exerts an inhibitory effect on transfection by the cationic lipids (in vitro, ex vivo or in vivo). The results presented in the examples show that the process of the invention can make it possible, by preliminary heating of the lipid, to enhance the transfection efficiency in the presence of serum. Thus, the compositions according to the invention possess a transfection efficiency which is as good in the presence as in the absence of serum.

The nucleic acid can be brought into contact with the lipid solution directly after obtaining the micellar solution, and the nucleolipid complex obtained used directly for cell transfection. The advantage of such compositions lies in particular in their homogeneous, defined and reproducible character. However, the applicant has also shown that to further enhance the properties of the compositions, in particular the transfection properties, it is advantageous to bring about the maturation of the cationic lipid before bringing into contact with the nucleic acid (pre-compaction maturation) and/or of the nucleolipid complex after bringing into contact (post-compaction maturation). The maturation of the lipid/complex makes it possible to reorganize the cationic lipid from the point of view of its structure and of its size. The applicant has indeed shown that a lipid in micellar solution as obtained during the first stage of the process of the invention can evolve to form organized bodies of different size and structure. The applicant has also shown that the state of organization of the cationic lipid had an influence on its capacity to complex (or to compact) the nucleic acids, as well as on its transfection properties.

A process of the invention comprises in addition, between the heating step and the bringing into contact, a step of pre-compaction maturation of the lipid vector.

A process of the invention comprises in addition, after the bringing into contact, a step of post-compaction maturation of the nucleolipid complex.

Starting with a micellar solution, it is possible, by promoting the interactions between the various lipid molecules and the supramolecular reorganization, to form different organized bodies. The examples presented below show, in particular, that the cationic lipids pass through unexpected organized states of the micellar, tubular or vermicular type. When the concentration is increased, larger size states appear, such as columnar or hexagonal states. These different structures have different properties.

To carry out the invention, a pre-compaction maturation step is advantageously carried out. This step is advantageously carried out until organized aggregates of the lamellar, tubular, vermicular, columnar and/or hexagonal type appear. More preferably, this step is carried out until organized aggregates of the lamellar, tubular and/or vermicular type appear. This type of body has, indeed, a novel structure most particularly appropriate for the formation of a complex with nucleic acids.

The maturation can be carried out by any means which makes it possible to increase the interactions between the molecules of cationic lipid, or to promote intramolecular reorganization. According to the invention, the maturation is advantageously carried out by decreasing the temperature, increasing the pH of the medium and/or increasing the ionic strength of the medium.

Figure 2:
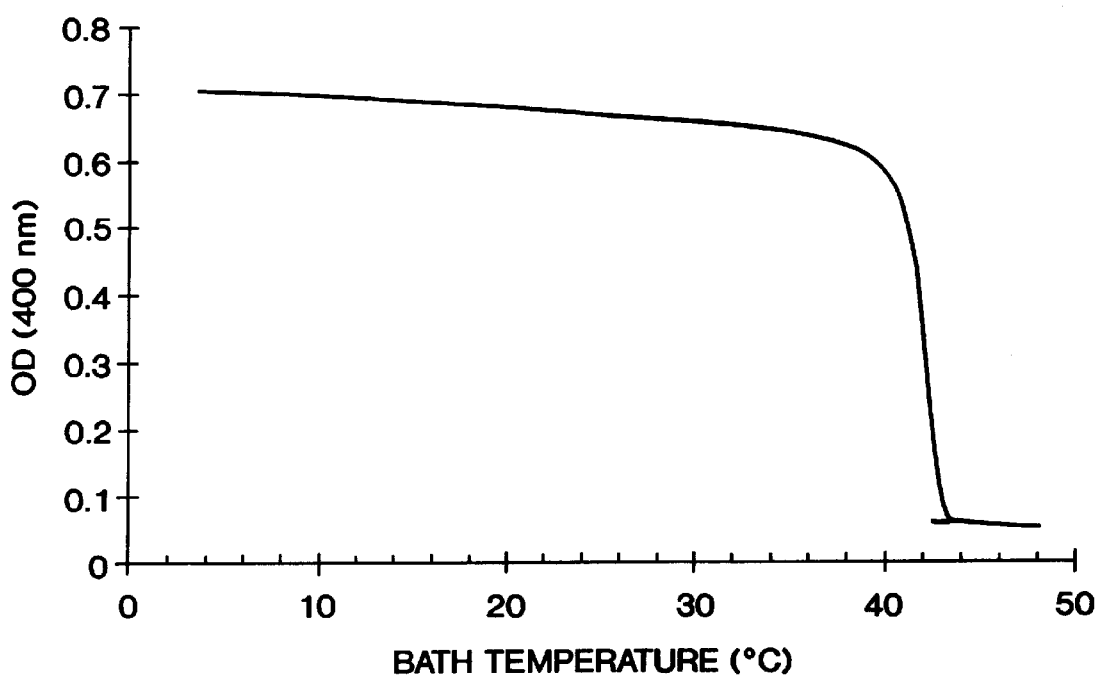
Figure 3A:
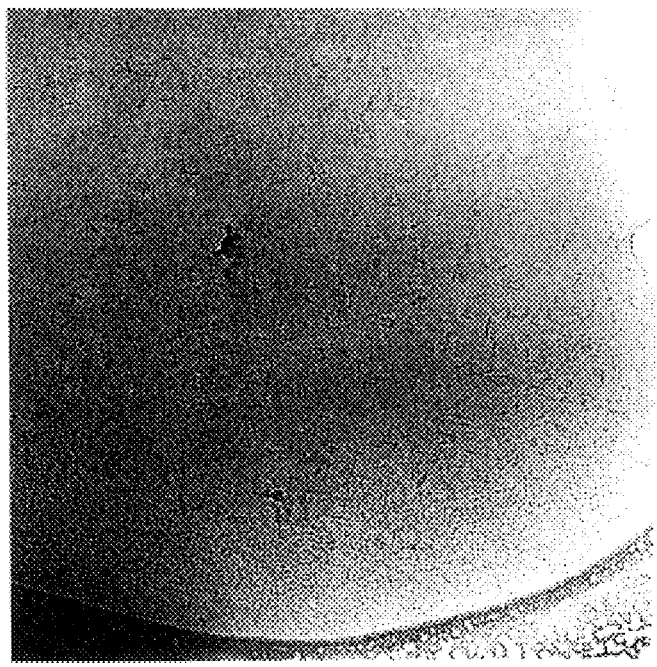
Figure 3B:
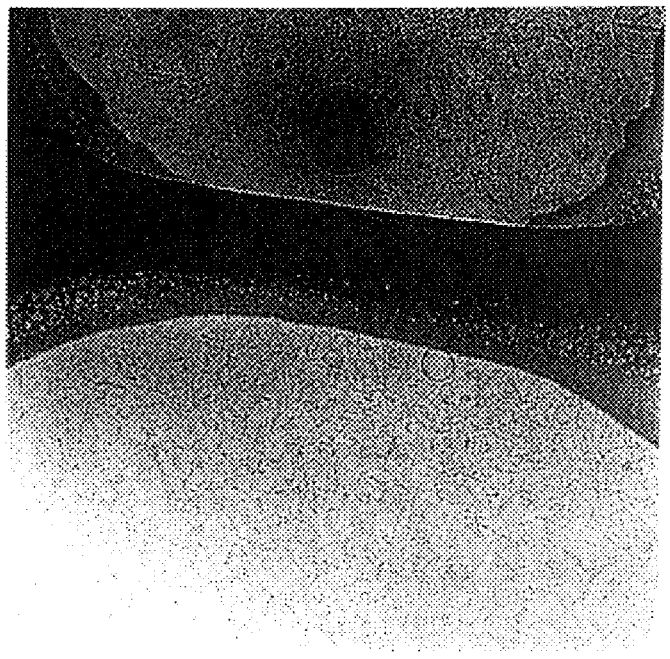
Figure 3C:
Figure 3D:
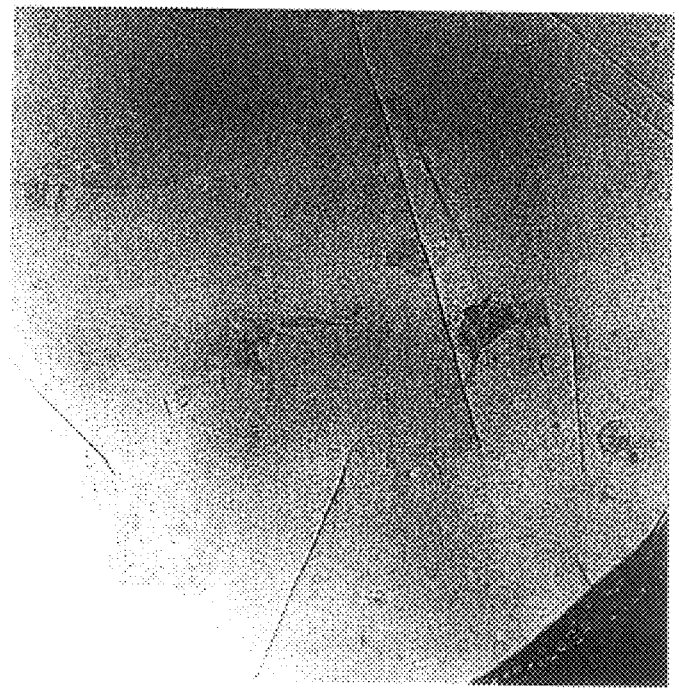
Figure 4:
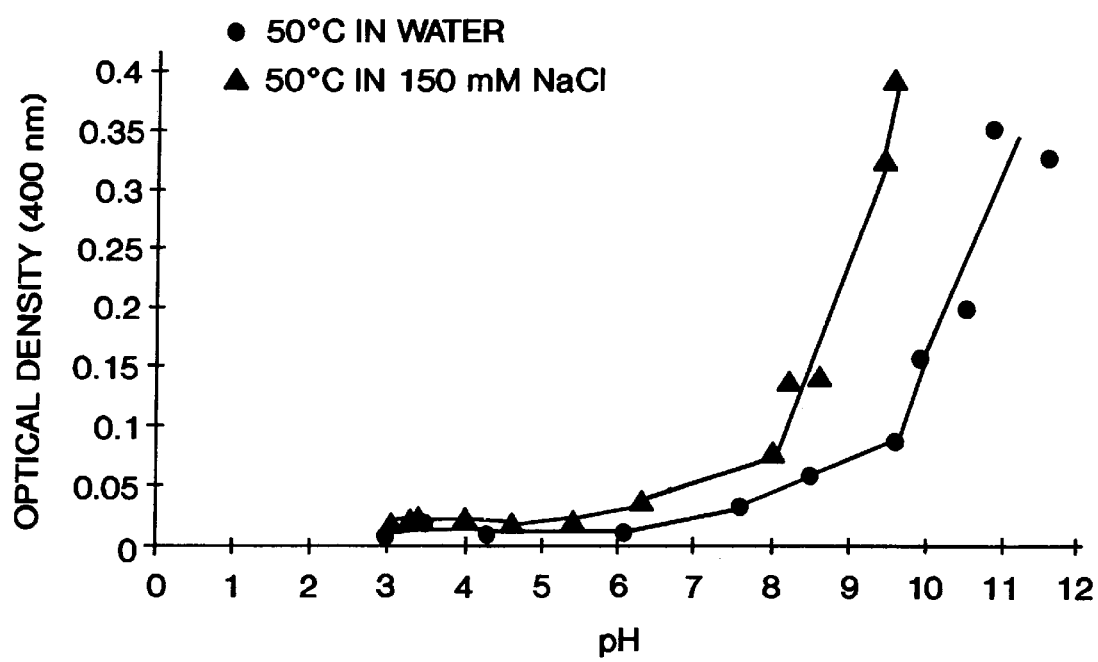

By decreasing the temperature, the aliphatic fatty chains reorganize and make it possible to restructure the cationic lipid. The results presented in FIG. 2 show the clear variation of the optical density of a solution of lipid, reflecting the internal architecture of the said lipid, as a function of the temperature of the medium. By increasing the pH or the ionic strength of the medium, it is possible to modify the state of the positive ionic charges present on the cationic part of the vector. Thus, by progressively neutralizing (pH) or protecting (shielding, ionic strength) the charges, the applicant has shown that the electrostatic forces of repulsion between the lipid molecules were progressively and controllably reduced, and that interactions and the reorganization into structured aggregates were promoted. The results presented in FIGS. 4 and 5 show the effect of the pH and of the ionic strength on the state of organization of the lipid. The photographs presented in FIG. 3 illustrate the various bodies demonstrated.

Advantageously, the pre-compaction maturation is carried out by decreasing the temperature. Still more preferably, it is carried out by incubating the solution at room temperature. This allows gradual and slow maturation kinetics (of aggregation and of reorganization), appropriate for the compaction with nucleic acids. The maturation can be continued for a variable duration depending on the lipid and depending on the pH and ionic strength conditions. The examples below show that this maturation can be carried out over a period ranging from a few hours to one month. The duration of the pre-compaction maturation is determined in particular by the appearance of structured bodies of the lamellar, tubular or vermicular type. However, if the pH and/or the ionic strength during the condensation step are sufficiently high, and/or if a post-compaction maturation is carried out, it is advantageous not to carry out a pre-compaction maturation. The micellar form of the lipid indeed allows in this case the production of nucleolipid complexes which are smaller and more homogeneous in size, and which are more efficient for the transfection in the presence or in the absence of serum.

The maturation can also be carried out by increasing the ionic strength of the medium. In this regard, it is advantageous to work, either during the solubilization, or during the maturation, or during the bringing into contact (compaction), in a solution having an ionic strength of between 0 and 0.5 M. Preferably, a solution is used which is nearly isotonic (0.15 M), that is to say an ionic strength of between 0.05 and 0.2 M. Various salts can be used (NaCl, $KNO_3$, KI and the like).

Moreover, it is also possible to vary the pH during the maturation phase. It is advantageous, during the maturation or during the compaction, to work in a pH zone of between 3 and 9, preferably between 6 and 9. The pH is of course adjusted by persons skilled in the art according to the pK values of the lipid vectors used and the phase diagram for the lipid. An advantageous pH zone is that in which at least 30% of the amines of the cationic vector are deprotonated, preferably at least 40%.

In general, independently of the pH and the ionic strength, the pre-compaction maturation is carried out by decreasing the temperature below the phase transition temperature of the lipid. This decrease may be accompanied by pH and ionic strength modifications, either during the maturation, or during the compaction itself.

By way of illustration, under intermediate pH and ionic strength conditions (for example for DOGS in 150 mM NaCl at a pH$\leq$8), the following states of organization are observed:

A suspension of DOGS in 150 mM NaCl at pH 7.5 is composed:
essentially of spherical micelles, immediately after heating to about 50° C. (FIG. 3A),
of spherical micelles of small rods and of vermicules of variable length, three hours after heating and cooling to room temperature (FIG. 3B),
of platelets of lamellar structure whose size is variable, one week after heating and cooling to room temperature (FIG. 3C),
solely of large plates of lamellar structure, one month after heating and cooling to room temperature (FIG. 3D).

At a native pH (about 3.5), the same suspension is composed of spherical micelles and of vermicules one day after heating and cooling to room temperature.

In DMEM medium adjusted to pH 5, a suspension of DOGS is composed:
solely of spherical micelles, immediately after heating,
of spherical micelles and of vermicules, 5 hours or one week after heating and cooling to room temperature.

These observations show how the maturation time can be adjusted according to the lipid and the medium conditions to form organized aggregates of the lamellar or vermicular type. Since it is now possible to know the structure adopted by the lipid according to the medium conditions and the time after heating, it is acceptable to control the lipid structure which is subsequently brought into contact with DNA. Moreover, the reversibility of the heating/cooling/"pre-compaction maturation" process is total. Regardless of the maturation time taken, it is therefore possible to reheat the suspension in order to return to a micellar state common to all conditions.

After the heating step and the optional pre-compaction maturation, the lipid is brought into contact with the nucleic acid.

The nucleic acid may be a DNA or an RNA. It may be a linear or circular, supercoiled or relaxed DNA of the plasmid type or otherwise, carrying various genetic elements (coding phase, promoters, terminators, binding sites, replication origins and the like). The nucleic acid may be of various origins (human, animal, lower eukaryotic, prokaryotic, plant, viral, phage and the like). It may also be a synthetic or semi-synthetic nucleic acid. The size of the nucleic acid may be highly variable (from an oligonucleotide to a complete genome). The advantage of the compositions of the invention lies, in addition, in their application to the transfer of nucleic acids of any size. According to a specific embodiment, the nucleic acid is a DNA (for example a plasmid or a DNA fragment) carrying a cassette for expressing a protein or a specific RNA. This may be a therapeutic or food protein (enzyme, amino acid and the like), for producing the said protein or the said RNA in vitro, ex vivo or in vivo. In addition, the nucleic acid used may be a mixture of different nucleic acids, having different properties.

The nucleic acid can be prepared by any technique known to persons skilled in the art (screening of a library, artificial synthesis, mixed methods, and the like).

For the bringing into contact (compaction), the nucleic acid (the nucleic acid composition) is solubilized in an aqueous medium. The composition, the ionic strength and the pH of this medium can be adjusted so as to enhance the efficiency of the compaction and the transfer properties of the final compositions. In particular, it has been observed in the studies carried out with DOGS that a compaction carried out in a medium where the lipid could be present in the micellar state during its contacting with the DNA (that is to say in a medium of very low ionic strength and/or of low pH), and this regardless of its state preceding the stage of bringing into contact, did not allow good transfection efficiency in the presence of foetal calf serum. It has been shown that the structure of the complexes formed under these low pH and ionic strength conditions is not of the lamellar type. Thus, advantageously, the compaction is carried out in a saline medium, in a pH zone of between 4 and 10. The optimum conditions depend on the lipid and in particular on its capacity to adopt, in the presence of nucleic acid, lamellar-type phases. Advantageously, the compaction is carried out in a medium having a pH of between 6 and 9. As regards the salinity of the medium, it is advantageously between 0 and 2 M, preferably between 0.01 and 0.5 M, still more preferably between 0.05 and 0.2 M. An advantageous medium for the compaction is a medium which is nearly isotonic (0.15 M), whose pH is between 6 and 9. These conditions may be those of the medium for heating the lipid or those for the pre-compaction maturation. Under these conditions, the compaction can take place without modification of the medium. If the pre-compaction maturation conditions are different, it is advantageous to adjust the composition of the medium as indicated above. The results presented in the examples indeed show that, under these conditions, it is possible to obtain compositions having particularly unexpected and advantageous transfection properties. In particular, it is possible to obtain compositions insensitive to the inhibitory effect of serum, which is particularly advantageous for in vitro (FCS) or in vivo uses.

For the bringing into contact, the respective quantities and concentrations of nucleic acid and of lipid can vary. These quantities and concentrations are those described in the prior art for the use of these vectors. In particular, the respective quantities of nucleic acid and of lipid used are determined by the ratio of positive charges of the lipid to the negative charges of the nucleic acid. This charge ratio can vary within a range of 0.01 to 100, and can be adjusted by persons skilled in the art according to the lipid selected, the nucleic acid selected, and depending on whether the use is of the in vitro or in vivo type. Advantageously, it is between 0.01 and 20.

The nucleolipid complex thus obtained can be used as such for the transfection. It can also be subjected to a so-called "post-compaction" maturation, which makes it possible to optimize the structural organization of the complex so as to enhance its transfer properties. Indeed, the states of organization of the lipids which allow good compaction with the nucleic acid are not necessarily those which give the best transfection levels. Thus, it is advantageous to carry out a post-compaction maturation until organized aggregates of the lamellar, columnar and/or hexagonal type appear. When such aggregates are initiated during the compaction, it may be advantageous to carry out a post-compaction maturation in order to homogenize the composition. The post-compaction maturation conditions and means are similar to those for the pre-compaction maturation. The duration of this maturation is adjusted by persons skilled in the art according to the pre-compaction maturation and the lipid vector.

The compositions obtained can be used immediately after preparation for the transfer of nucleic acids. They can also be stored and preserved, for example, in freeze-dried or frozen form, for subsequent use. As indicated above, the compositions of the invention have numerous advantages for industrial use. They are calibrated, homogeneous, reproducible, stable and offer high transfer capacities.

One subject of the invention consists in particular in a composition for the transfer of nucleic acids comprising a nucleic acid complexed with a cationic lipid, characterized in that the transfer efficiency is practically unaltered by the presence of serum and in that it can be obtained by the process described above.

The composition preferably comprises, as cationic lipid, a lipopolyamine. Still more preferably, this is a lipothermine or a lipospermine, preferably having 2 fatty chains. Moreover, certain adjuvants can be added to the compositions, in particular lipid adjuvants. More preferably, the lipid adjuvants are neutral lipids having 2 fatty chains.

In a particularly advantageous manner, natural or synthetic lipids, which are zwitterionic or which lack an ionic charge under physiological conditions, are used. They may be chosen more particularly from dioleoylphosphatidylethanolamine (DOPE), oleoyl-palmitoylphosphatidylethanolamine (POPE), di-stearoyl, -palmitoyl, -myristoyl phosphatidylethanolamine as well as their 1- to 3-times N-methylated derivatives; phosphatidylglycerols, diacylglycerols, glycosyldiacylglycerols, cerebrosides (such as in particular galactocerebrosides), sphingolipids (such as in particular sphingomyelins), cholesterol or alternatively asialogangliosides (such as in particular asialoGM1 and GM2).

These various lipids can be obtained either by synthesis, or by extraction from organs (example: the brain) or from eggs, by conventional techniques well known to persons skilled in the art. In particular, the extraction of the natural lipids can be carried out by means of organic solvents (see in particular Lehninger, Biochemistry).

Preferably, the compositions of the invention comprise, in addition to the cationic lipid, from 0.1 to 20 molar equivalents of neutral lipid for 1 molar equivalent of nucleic acid phosphate, and more preferably from 1 to 5.

In a particularly advantageous embodiment, the compositions of the present invention comprise a targeting element which makes it possible to orient the transfer of the nucleic acid. This targeting element may be an extracellular targeting element, which makes it possible to orient the transfer of the nucleic acid towards certain cell types or certain desired tissues (tumour cells, hepatic cells, haematopoietic cells and the like). It may also be an intracellular targeting element, which makes it possible to orient the transfer of the nucleic acid towards certain selected cellular compartments (mitochondria, nucleus and the like).

More preferably, the targeting element is linked to the lipid covalently or noncovalently. The binding can in particular be obtained by ionic interaction with ammoniums, or by nucleophilic attack of the amines of the vector on targeting elements comprising a nucleofuge group (halogen, tosylate and the like), an activated ester (hydroxysuccinimide and the like) or alternatively an isothiocyanate. The targeting element can also be linked to the nucleic acid.

Among the targeting elements which can be used within the framework of the invention, there may be mentioned sugars, peptides, oligonucleotides or lipids. Preferably, they are sugars and/or peptides such as antibodies or antibody fragments, ligands of cell receptors or fragments thereof, receptors or receptor fragments, and the like. In particular, they may be receptor ligands, growth factors, cytokine receptors, cellular lectin receptors or adhesion protein receptors. There may also be mentioned the receptor for transferrin, for the HDLs and for the LDLs. The targeting element may also be a sugar which makes it possible to target the asialoglycoprotein receptors, or alternatively a Fab fragment of antibodies which makes it possible to target the receptor for the Fc fragment of the immunoglobulins.

The transfectant compositions described can be used for the transfer of nucleic acids in vitro, ex vivo or in vivo. For applications in vivo, they may be formulated for administrations by the topical, cutaneous, oral, rectal, vaginal, parenteral, intranasal, intravenous, intramuscular, subcutaneous, intraocular or transdermal route and the like. Preferably, they contain a pharmaceutically acceptable vehicle for an injectable formulation, in particular for a direct injection at the level of the desired organ, or for administration by the topical route (on the skin and/or the mucous membrane). This may be in particular isotonic sterile solutions or dry, in particular freeze-dried, compositions which, upon addition, depending on the case, of sterilized water or of physiological saline, allow the preparation of injectable solutions. The nucleic acid doses used for the injection as well as the number of administrations can be adjusted as a function of various parameters, and in particular as a function of the mode of administration used, the relevant pathology, the gene to be expressed, or alternatively the desired duration of the treatment.

In this regard, another subject of the invention relates to a process for the transfer of nucleic acid into cells in vitro, in vivo or ex vivo comprising bringing the said nucleaic acid into contact with a previously heated cationic lipid suspension, and incubating the cells with the resulting nucleolipid complex.

Advantageously, the cationic lipid suspension is previously heated and matured. However, according to a preferred mode, the nucleolipid complex is matured prior to the incubation with the cells. The incubation with the cells can take place in vivo, on an appropriate support (culture dish, pouch, flask and the like) optionally under sterile conditions. The quantities of DNA incubated are known to a person skilled in the art (in the microgram range per $10^6$ cells). For a use in vivo, the incubation can be carried out by administering the composition in vivo (local or systemic for example).

Figure 1B:
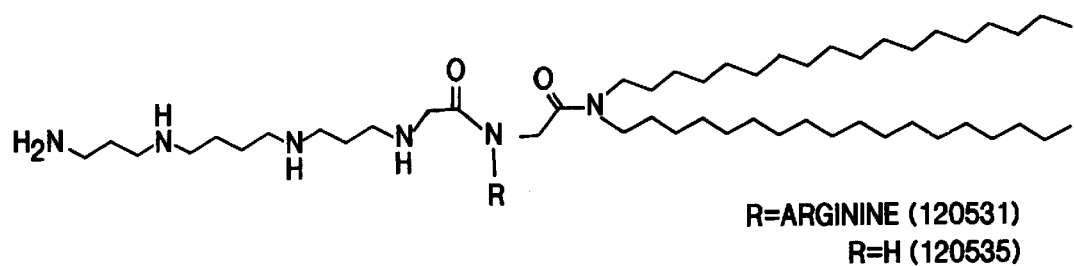

The present invention will be described more fully with the aid of the following examples which should be considered illustrative and non-limiting. Legend to the figures:

FIGS. 1A and 1B: Chemical structures of the cationic lipids, 1A: DOGS, 1B: RPP120531 and RPR120535.

FIG. 2: Influence of the temperature on the optical density at 400 nm of a 1 mM suspension of DOGS in NaCl.

FIGS. 3A–3D: Transmission cryo-microscopy micrograph of a 2 mM suspension of DOGS in NaCl at pH 7.5. The sample was prepared immediately after heating (3A), 3 hours (3B), 1 week (3C) and 1 month (3D) after heating the suspension and cooling to room temperature.

FIG. 4: Influence of the pH on the optical density at 400 nm of a 0.6 mM suspension of DOGS in water or in 150 mM NaCl. Study temperature: 50° C.

FIGS. 5A–5F: Phase diagrams for DOGS (5A: water; 5B: 150 mM NaCl), for RPR120531 (5C: water; 5D: 150 mM NaCl) and for RPR120535 (5E: water; 5F: 150 mM NaCl).

Figure 6:
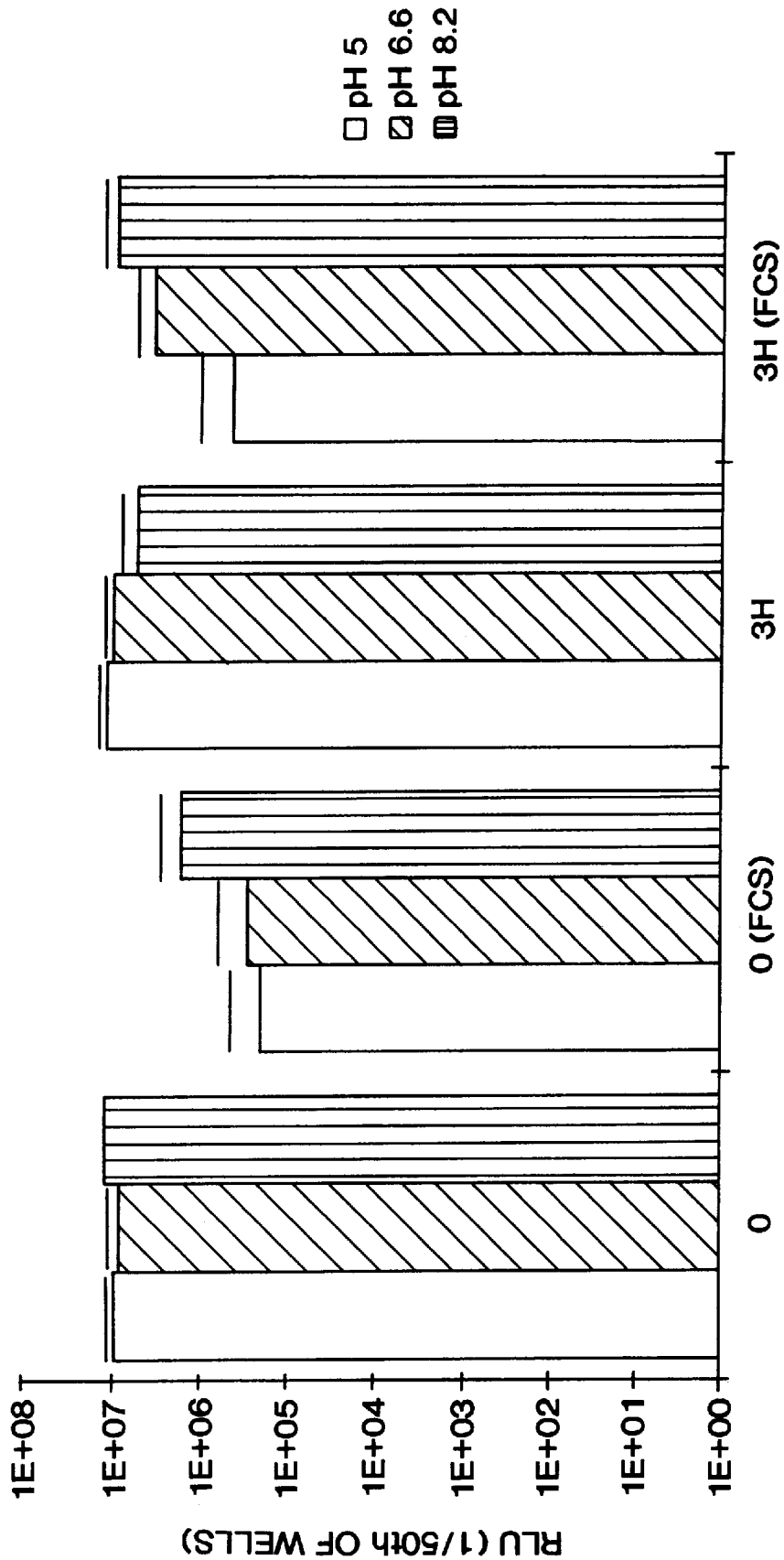

FIG. 6: Transfectant power of the compositions of Example 5

Figure 7:
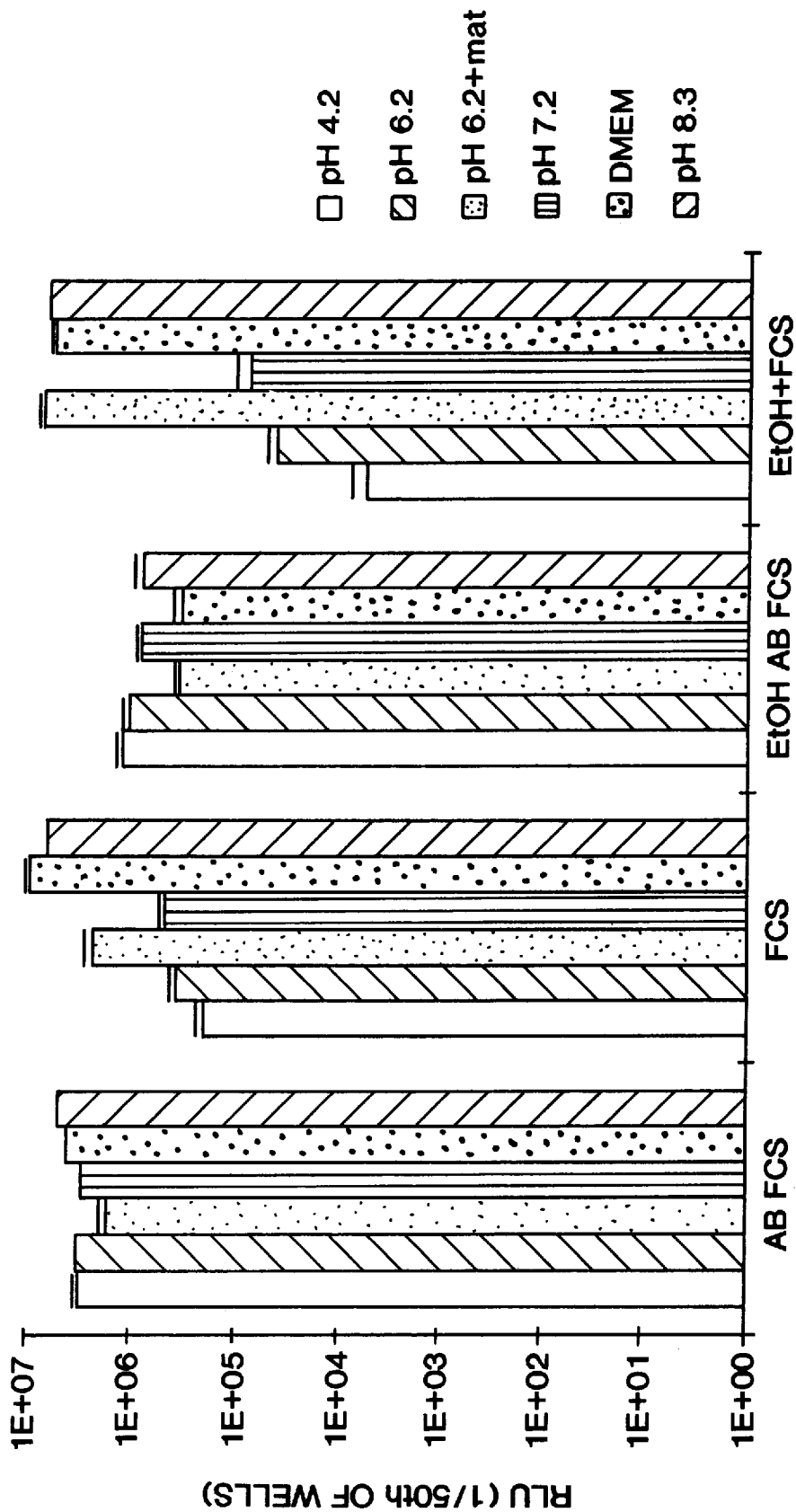

FIG. 7: Transfectant power of the compositions of Example 6

Figure 8:
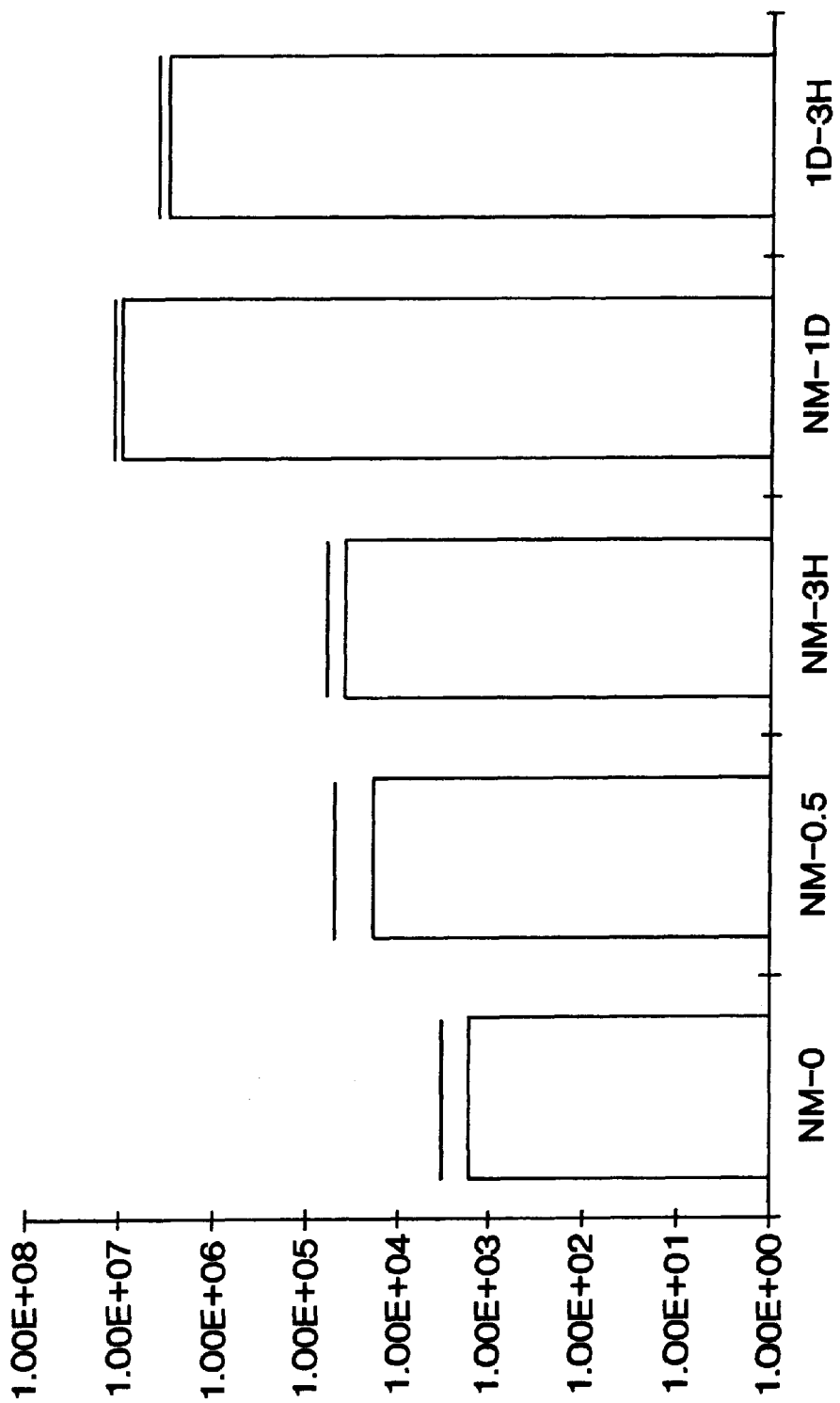

FIG. 8: Transfectant power of the compositions of Example 7

Figure 9:
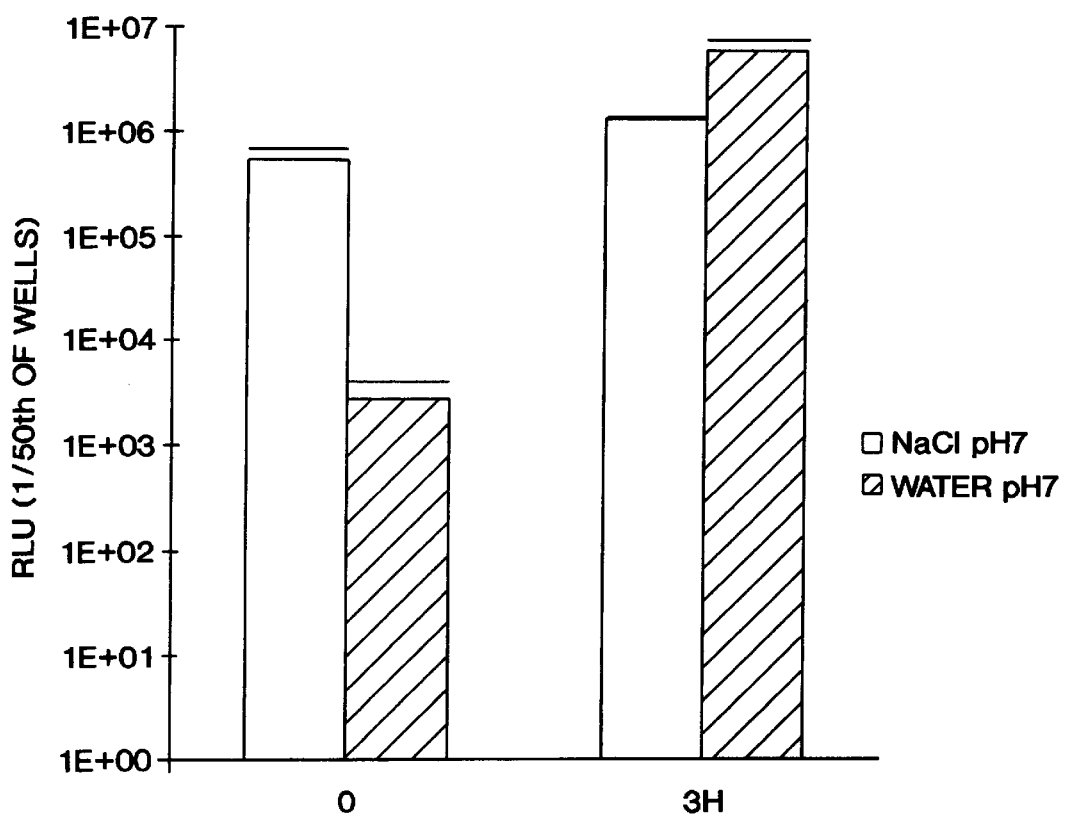

FIG. 9: Transfectant power of the compositions of Example 8

Figure 10:
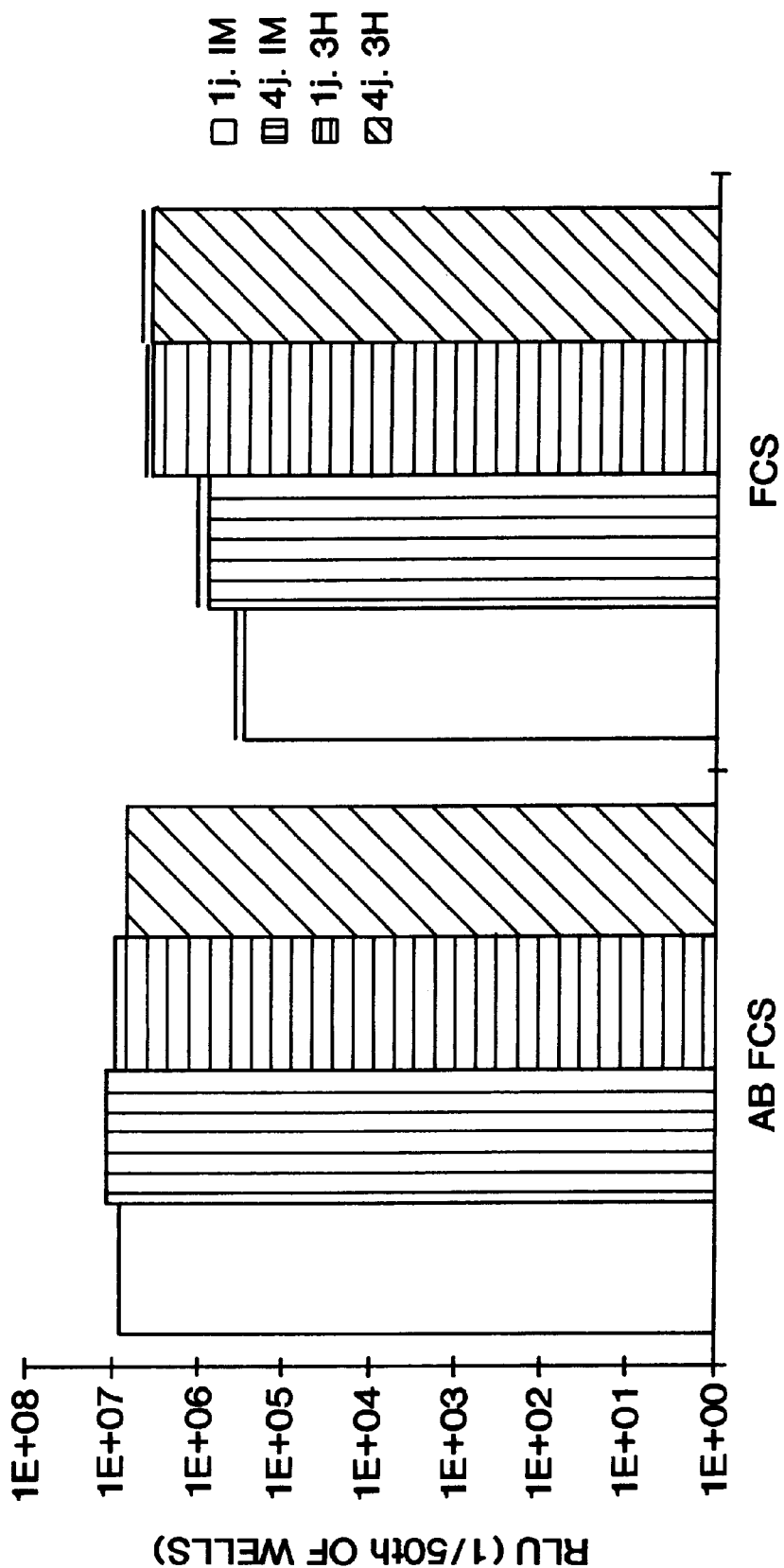

FIG. 10: Transfectant power of the compositions of Example 9

Figure 11:
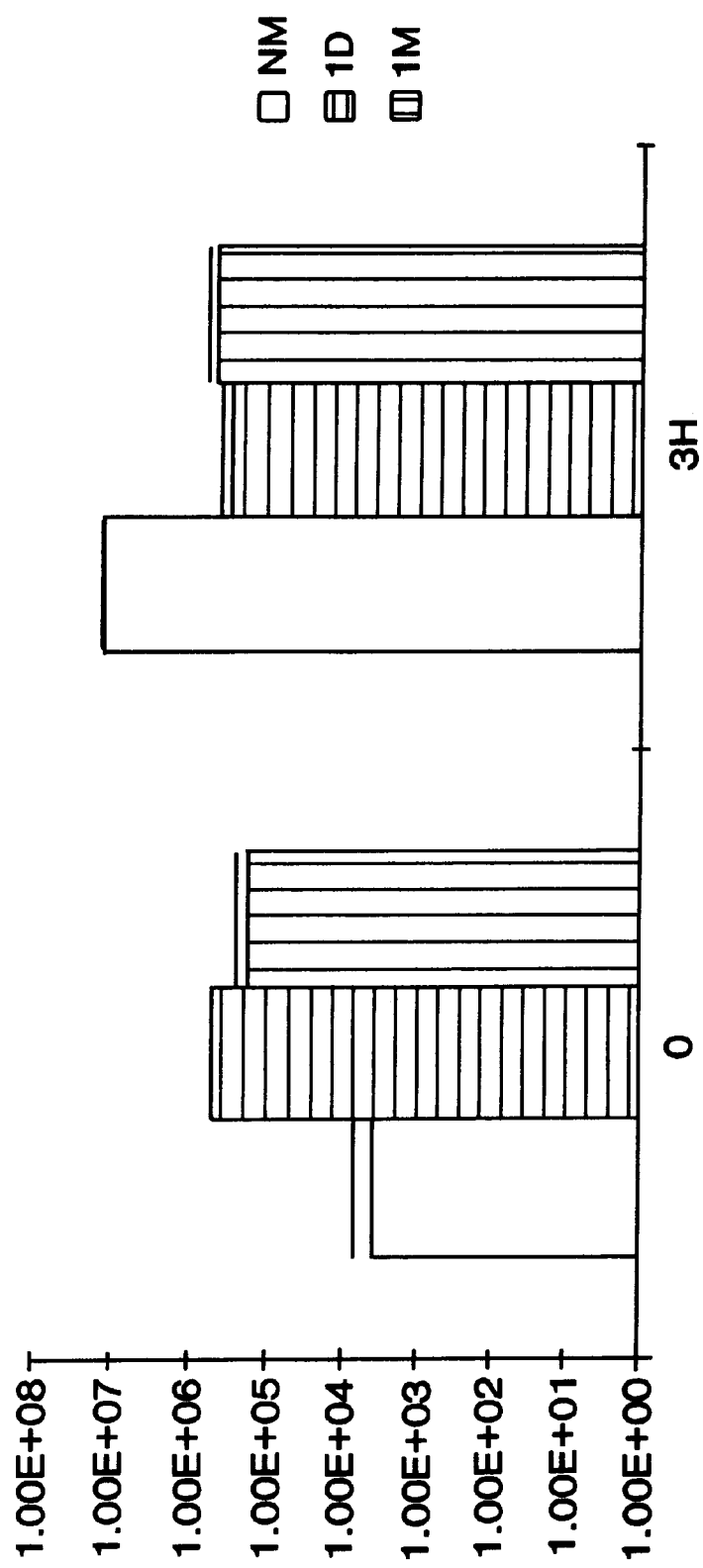

FIG. 11: Transfectant power of the compositions of Example 10

Figure 12:
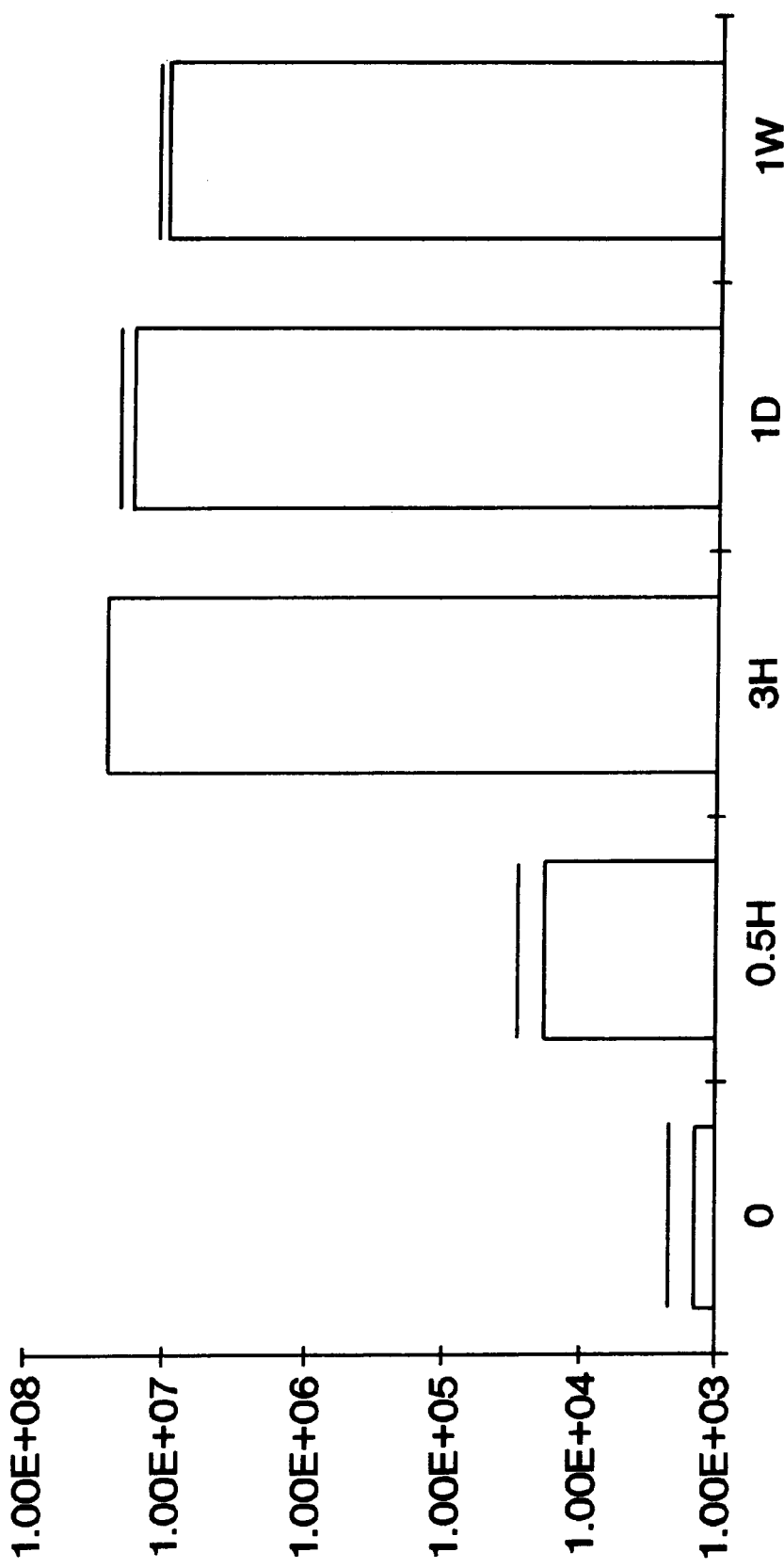

FIG. 12: Transfectant power of the compositions of Example 11

MATERIALS AND METHODS

1. The plasmid used in the following examples (pXL2784) is a ColE1 derivative carrying the kanamycin resistance gene, and the cer fragment of ColE1. The eukaryotic expression cassette contains the CMV promoter of the plasmid pCDNA3 controlling the gene encoding luciferase (*Photinus pyralis*). It is understood that any other nucleic acid can be used.

2. The cationic lipids used in the following examples are DOGS, RPR120531 and RPR120535 whose structure is represented in FIG. 1. It is understood that the same experiments can be carried out with other cationic lipids.

3. Transfection protocol. The procedure described is applicable for transfections in vitro, ex vivo and in vivo. The cells used are murine fibroblasts NIH 3T3, inoculated the day before in 24-well plates, at a density of 50,000 cells per well. The culture medium used is the DMEM medium (Dulbecco's Modified Eagle Medium), containing 4.5 g/l of glucose, supplemented with 10% foetal calf serum, 1% L-glutamine (200 mM stock solution), 1% sodium pyruvate, streptomycin (5000 IU/ml) and penicillin (5000 µg/ml) (Gibco). Prior to the transfection, the cells are rinsed twice with DMEM free of foetal calf serum. The transfection of the cells is carried out with 50 µl of a transfection suspension containing 0.5 µg of DNA and 3 nmol of DOGS per well, in 200 µl of culture medium supplemented or otherwise with 10% foetal calf serum. After incubating for 4 hours at 37° C. (in a $CO_2$ incubator), the culture medium containing the nucleolipid complex is removed and replaced with 500 µl of DMEM supplemented with 10% foetal calf serum. The cells are then incubated for 48 hours.

4. Measurement of the luciferase activity of eukaryotic cells. It is carried out 48 hours after transfection. Luciferase catalyses the oxidation of luciferin, in the presence of ATP, $Mg^{2+}$ and $O_2$, with the concomitant production of a photon. The total light emission, measured by a luminometer, is proportional to the luciferase activity in the sample. The reagents used are provided by Promega (luciferase assay system) and used according to a recommended protocol. After a double rinsing of the cells with PBS, the cells are lysed with 250 µl of lysis buffer and the insoluble fraction of each extract is removed by centrifugation. The assay is carried out on 5 µl of supernatant, diluted or otherwise in the cell lysis buffer.

EXAMPLES

Example 1

Influence of the Temperature on the Molecular Organization of the Cationic Lipids A 1 mM colloidal solution of DOGS was prepared by dissolving crystallized DOGS in chloroform, evaporating the solvent and drying in a freeze-drying apparatus. The film is then taken up in a buffer solution containing 0.9% NaCl (Hepes 10 mM, pH 7.4). After heating to 50° C., the colloidal solution was placed at 4° C. for one week. The optical density is monitored continuously (lambda 2 spectrophotometer (Perkin Elmer) with a thermostatted cuvette holder), while the temperature of the bath (LAUDA RM6), itself connected to the spectrophotometer cuvettes, varies at a determined and controlled speed of 1.25° C./min. The cuvette containing the sample is equipped with a stirring system.

The results obtained are presented in FIG. 2. They show a sharp drop in the optical density at around 40° C. approximately. This drop in OD reflects a profound rearrangement of the structure of the lipid.

In parallel, the physical state of the DOGS during these temperature variations was studied by transmission cryomicroscopy. For that, a 2 mM suspension of DOGS in NaCl at pH 7.5 was heated to 50° C. The physical nature of the objects was determined after heating over time, during the maturation by incubating at room temperature. The results obtained are presented in FIG. 3: the preparation of the sample was carried out immediately after heating (3A), 3 hours (3B), 1 week (3C) and 1 month (3D) after heating the suspension and cooling to room temperature.

The results obtained show a variation in the structure of the DOGS, from the micellar state up to the formation of lamellar bodies, via structures in the form of rods and vermicules. This example makes it possible to define conditions for pre-compaction maturation of the lipid.

Example 2

Influence of the pH on the Molecular Organization of the Cationic Lipids

A 1 mM colloidal solution of DOGS was prepared by dissolving crystallized DOGS in chloroform, evaporating the solvent and drying in a freeze-drying apparatus. The film was then taken up in a 150 mM solution of NaCl or in water, in a pH range of 3.0 to 11.0. After heating to 50° C., the suspensions are placed at room temperature (25° C.) at least 3 hours before the start of the measurement. The optical density is determined under the conditions described in Example 1.

The results obtained are presented in FIG. 4. They show very clearly an increase in the optical density as a function of the pH. This increase reflects an increase in the interactions between the lipid molecules, due to a decrease in the electrostatic repulsions.

Example 3

Phase Diagrams for the Cationic Lipids

To validate the observations made in Examples 1 and 2, phase diagrams were plotted for different lipid vectors. These diagrams describe the physical state of the lipids depending on the pH, ionic strength and temperature conditions. They also show the phase transition temperatures and the aggregative behaviour of the lipid as a function of its ionization state.

Figure 5A:
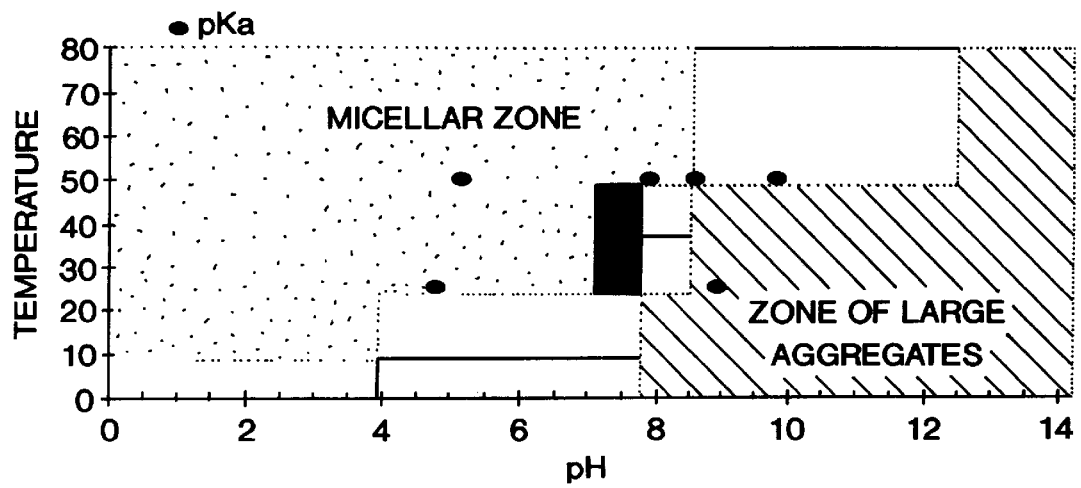
Figure 5B:
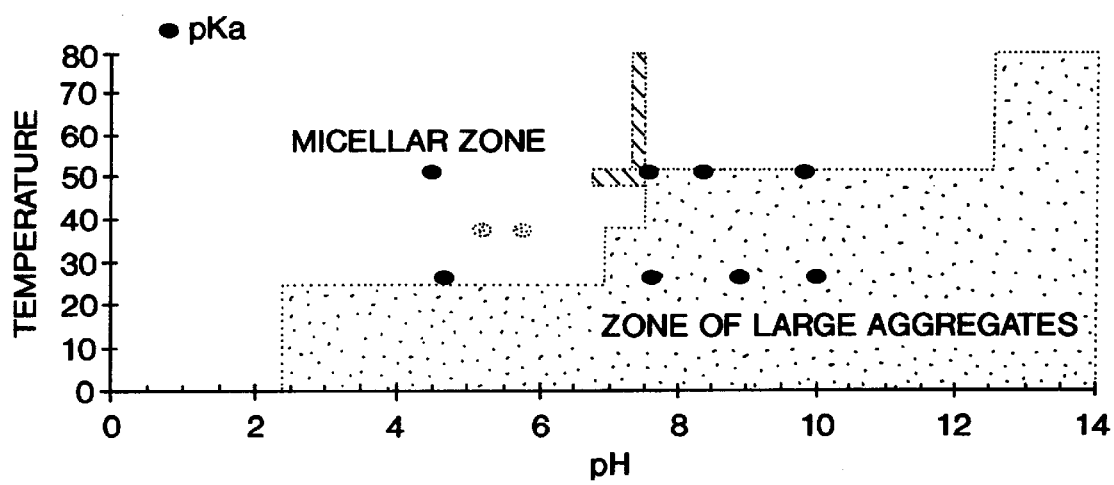
Figure 5C:
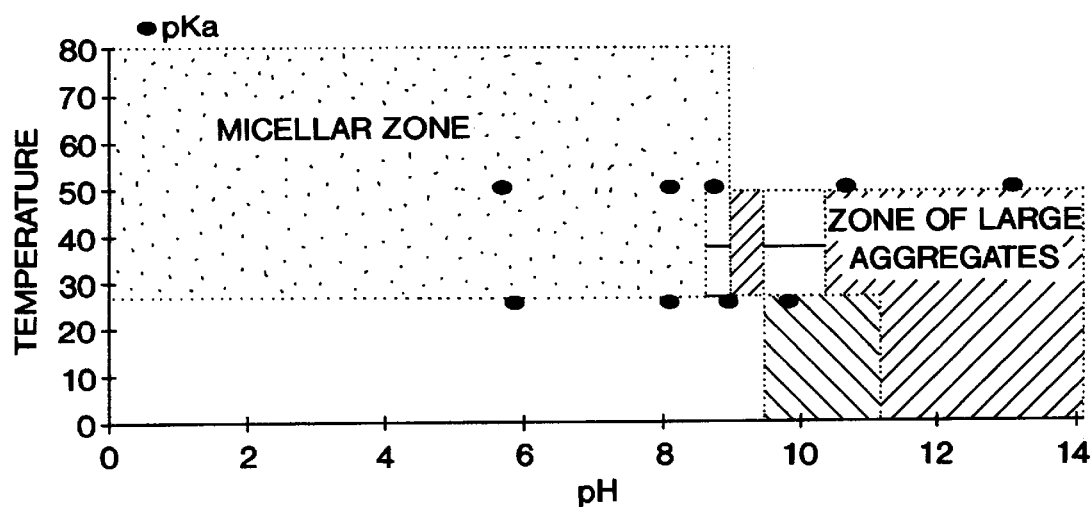
Figure 5D:
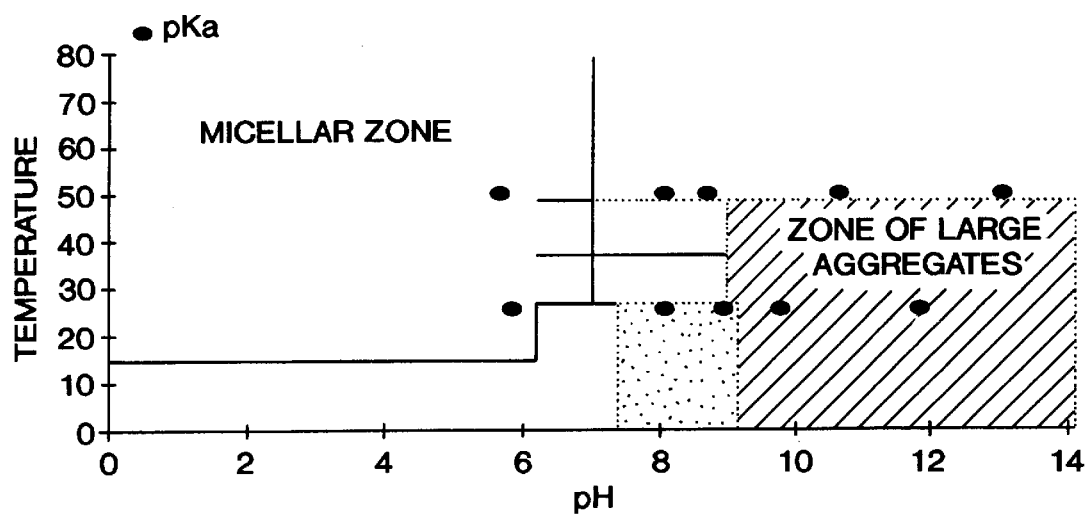
Figure 5E:
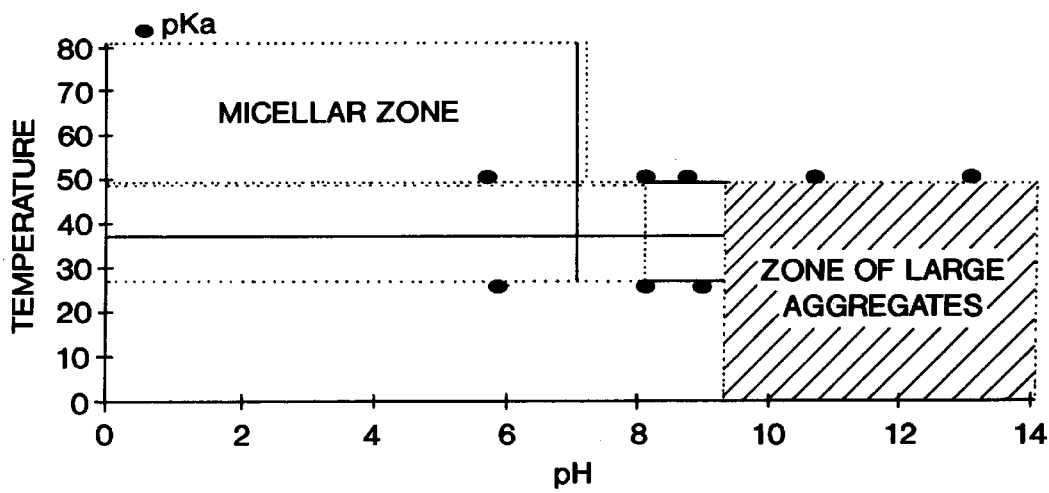
Figure 5F:
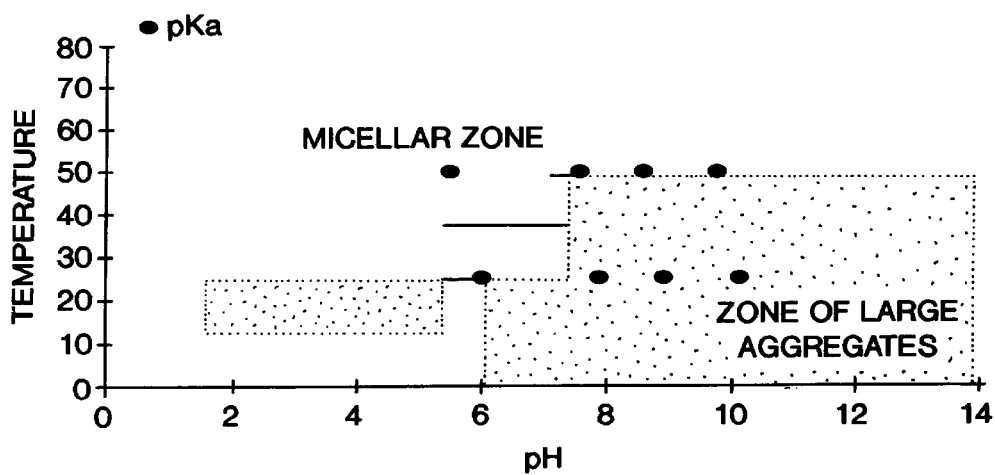

These diagrams are presented in FIGS. 5A and 5B for DOGS, 5C and 5D for RPR120531 and 5E and 5F for RPR120535. They show that in the case where the lipid is solubilized in pure water (pH≦6), the micellar solution obtained by heating according to the invention is stable. They also make it possible to define the ionic strength and pH conditions for which the micellar solution is stable over time.

Example 4

Study of Various Counter-Ions in the Base Electrolyte

Various counter-ions were tested in the maturation stage. For that, various suspensions of DOGS in a medium whose base electrolyte is present at a concentration of 0.1 M and whose pH is not adjusted (native pH: 3.5) were observed for one week after heating and cooling to room temperature:

In $KNO_3$, the nanometric structures are of the micellar type and a few rare marked edges are observed. The submicron structures are fine filaments with a high aggregative tendency.

In KI, the nanometric structures have the appearance of a superposition of lamellae whose edges appear highly marked. The submicron structures also exist in the form of filaments but whose thickness is greater and which has a lesser aggregative tendency.

Example 5

A. Protocol for the Preparation of the Complex and Transfection

The lipid (DOGS) is presented to the DNA in the form of a 2 mM suspension in 150 mM NaCl at native pH (3.5) heated and left at room temperature for 1 day before contacting with the DNa ("pre-maturation of 1 day"). The lipid is introduced into a suspension containing the plasmid pXL2784 and composed of 150 mM NaCl adjusted to a pH of 5–6.6 or 8.2 (these pH values are measured values). The "post-compaction maturation" is from 0 to 3 hours at room temperature and the transfection was carried out in the presence (FCS) and in the absence of foetal calf serum.

B. Results

The transfection results expressed in RLU (Relative Light Unit) per 5 µl of lysate, that is to say ⅕₀th of wells, are presented in FIG. 6. Each value is a mean of measurements on 4 wells. The standard deviations are represented by horizontal bars.

This study shows that by starting with a solution of vermicular micelles, a compaction in a saline medium of high pH (here 8.2) makes it possible to dispense with the inhibitory effect of the serum, regardless of the "post-compaction maturation". Moreover, when an intermediate compaction pH (still in saline medium) is used, "a post-compaction maturation" also makes it possible to dispense with the inhibitory effect of the serum on the transfection.

A similar study was carried out on the lipids RPR120531 and RPR120535 (see FIG. 1 for the structures of DOGS, RPR120531 and RPR120535). It shows a similar behaviour to that of DOGS in relation to the influence of the compaction pH and of the "post-compaction maturation" on dispensing with the serum effect.

Example 6

A. Protocol for the Preparation of the Complex and Transfection

The lipid (DOGS) is presented to the DNA either in the form of a 2 mM suspension in 150 mM NaCl at native pH (3.5) heated and left at room temperature for 1 day before contacting with the DNA ("pre-maturation of 1 day") or in the form of a 2 mM solution in ethanol (EtOH). The lipid is introduced into a suspension containing the plasmid pXL2784 and composed of 150 mM NaCl adjusted to a pH of 4.2–6.2–7.2 or 8.2 (these pH values are measured values) or alternatively into DMEM culture medium. No "post-compaction maturation" is carried out except in the case where the compaction is carried out at a pH of 6.2 (pH 6.2+mat.). In this case, the "post-compaction maturation" lasts for 3 hours at room temperature. The transfection was carried out in the presence (FCS) and in the absence of foetal calf serum (AB FCS).

B. Results

The transfection results expressed in RLU (Relative Light Unit) per 5 µl of lysate, that is to say ⅕₀th of wells, are presented in FIG. 7. Each value is a mean of measurements on 4 wells. The standard deviations are represented by horizontal bars.

This study shows that the behaviour of the compacted DNA particles in relation to the inhibition by foetal calf serum seen in Example 5 (as a function of the compaction pH and of the "post-compaction maturation") is also valid whether the DOGS is present in the form of a suspension in saline medium or in the form of an ethanolic solution. It also shows that the "post-compaction maturation" step makes it possible to dispense with the inhibition by the serum.

Example 7

A. Protocol for the Preparation of the Complex and Transfection

The lipid (DOGS) is presented to the DNA in the form of a 2 mM suspension in 150 mM NaCl at native pH (3.5) heated immediately (NM: for Not pre-Matured) before contacting with the DNA or "pre-matured" 1 day before compaction (1 D). The lipid is introduced into a suspension containing the plasmid pXL2784 and composed of 150 mM NaCl adjusted to a pH of 6.2 (this pH is a measured value). The "post-compaction maturation" lasts for 0–0.5 hour–3 hours–1 day when the lipid has not been "pre-matured"; it lasts for 3 hours when the lipid has been "pre-matured for 1 day" at room temperature (control). The transfection was carried out in the presence and in the absence of foetal calf serum. The results obtained in the absence of foetal calf serum not being significantly different according to the various protocols studied, only the results of the transfections carried out in the presence of foetal calf serum are represented.

B. Results

The transfection results expressed in RLU (Relative Light Unit) per 5 µl of lysate, that is to say ⅕₀th of wells, are presented in FIG. 8. Each value is a mean of measurements on 4 wells. The standard deviations are represented by horizontal bars.

This study shows that an absence of "pre-maturation" of the DOGS (heating immediately before bringing into contact with the DNA) requires increasing the "post-compaction maturation" time necessary for dispensing with the inhibitory effect of the serum. The structure adopted by the lipid before it is brought into contact with the DNA therefore appears to make it possible to accelerate the organization of the lipid-DNA complex.

It also appears that compaction carried out with a non-prematured lipid but followed by a sufficient "post-compaction maturation" time (IM-1 D) allows the formation of particles which are more efficient on the transfection than if the lipid was prematured (1 D–3 H), perhaps because the particles formed are smaller and of more regular size.

Example 8

A. Protocol for the Preparation of the Complex and Transfection

The lipid (DOGS) is presented to the DNA in the form of a 2 mM suspension either in water at pH 7.5 and "pre-matured" for 1 day before compaction (water 7.5), or in the form of a 150 mM suspension in NaCl at pH 7.5, also "pre-matured" for 1 day (NaCl 7.5). The lipid is introduced into a suspension containing the plasmid pXL2784 and composed of 150 mM NaCl adjusted to a pH of 7.2 (this pH is a measured value). The "post-compaction maturation" lasts for 0 (0) or 3 hours (3 H). The transfection was carried out in the presence of foetal calf serum.

B. Results

The transfection results expressed in RLU (Relative Light Unit) per 5 µl of lysate, that is to say ⅕₀th of wells, are presented in FIG. 9. Each value is a mean of measurements on 4 wells. The standard deviations are represented by horizontal bars.

These results show that it is possible to dispense with the inhibitory effect of the serum as well as with the "post-compaction maturation" by allowing the lipid before compaction to be more structured: conditions of higher pH and ionic strength in the case of NaCl 7.5 are indeed favourable to a certain type of organization. This study also shows that, when the "post-compaction maturation" takes place, it appears preferable for a good transfection efficiency to compact the DNA with a lipid whose particle size is not too large (water 7.5). For a good transfection efficiency in the presence of serum, it therefore appears that a compromise should be made between structuring of the lipid and size of the particles.

Example 9

A. Protocol for the Preparation of the Complex and Transfection

The lipid (DOGS) is presented to the DNA in the form of a 2 mM suspension in 150 mM NaCl at native pH (3.5) and "pre-matured" for 1 day before compaction (1 D) or 4 days before compaction (4 D). The lipid is introduced into a suspension containing the plasmid pXL2784 and composed of 150 mM NaCl adjusted to a pH of 6.6 (this pH is a measured value)y. The "post-compaction maturation" lasts for 0 (0) or 3 hours (3 H) The transfection was carried out in the presence (FCS) and in the absence of foetal calf serum.

B. Results

The transfection results expressed in RLU (Relative Light Unit) per 5 µl of lysate, that is to say 1/50th of wells, are presented in FIG. 10. Each value is a mean of measurements on 4 wells. The standard deviations are represented by horizontal bars.

This study shows no significant difference between the various protocols when the transfection is carried out in the absence of foetal calf serum. On the other hand, in the presence of serum, it is observed that a long "pre-maturation" (4 days) can make it possible to dispense in part with the inhibitory effect of the serum when a "post-compaction maturation" has not been carried out. This study also shows that when a "post-compaction maturation" is carried out, an additional "pre-maturation" proves unnecessary but not damaging, at least in the case of a pre-maturation in 150 mM NaCl at native pH, and for the "pre-maturation" times described above.

Example 10

A. Protocol for the Preparation of the Complex and Transfection

The lipid (DOGS) is presented to the DNA in the form of a 2 mM suspension in 150 mM NaCl at pH 7.5 and either heated immediately (IM), or "pre-matured" for 1 day (1 D), or "pre-matured" for 1 month (1 M) before the compaction. The lipid is introduced into a suspension containing the plasmid pXL2784 and composed of 150 mM NaCl adjusted to a pH of 7.2 (this pH is a measured value). The "post-compaction maturation" lasts for 0 (0) or 3 hours (3 H). The transfection was carried out in the presence of foetal calf serum.

B. Results

The transfection results expressed in RLU (Relative Light Unit) per 5 µl of lysate, that is to say 1/50th of wells, are presented in FIG. 11. Each value is a mean of measurements on 4 wells. The standard deviations are represented by horizontal bars.

This study shows that a "pre-maturation" makes it possible to dispense in part with the inhibitory effect of the serum on the transfection when a "post-compaction maturation" is not carried out. On the other hand, when a maturation of the nucleolipid complex is carried out, it is observed that the transfection efficiency obtained is better when the lipid has been heated immediately before it is brought into contact with the DNA and is therefore in the form of small lipid particles.

Example 11

A. Protocol for the Preparation of the Complex and Transfection

The lipid (DOGS) is presented to the DNA in the form of a 2 mM micellar solution in pure water (native pH of 3.5). The lipid is introduced into a suspension containing the plasmid pXL2784 and composed of 150 mM NaCl adjusted to a pH of 7.3 (this pH is a measured value). The "post-compaction maturation" lasts for 0 (0)–0.5 hour (0.5 H)–3 hours (3 H)–1 day (1 D) or 1 week (1 W). The transfection was carried out in the presence of foetal calf serum.

B. Results

The transfection results expressed in RLU (Relative Light Unit) per 5 µl of lysate, that is to say 1/50th of wells, are presented in FIG. 12. Each value is a mean of measurements on 4 wells. The standard deviations are represented by horizontal bars.

This study confirms that when DOGS is presented to the DNA in the form of a micellar solution, a "post-compaction maturation" becomes necessary in order to dispense with the inhibitory effect of the serum. It is observed, in the present case, that a "post-compaction" maturation of 3 hours proves sufficient.

All these results show that the process of the invention, involving a preliminary heating step and advantageous maturation steps, makes it possible to obtain defined, homogeneous and reproducible compositions which have enhanced transfectant properties.

BIBLIOGRAPHIC REFERENCES

Barthel F., Remy J. S. Loeffler J. P. and Behr J. P., Gene Transfer Optimization with Lipospermine-Coated DNA. *DNA Cell Biol.* 12, 533–560 (1993).

Behr J. P., Demeneix B., Loeffler J. P. and Perez-Mutul J., Efficient Gene Transfer into Mammalian Primary Endocrine Cells with Lipopolyamine-Coated DNA. *Proc. Natl. Acad. Sci. USA* 86: 6982–6986 (1989).

Bringham K. L., Meyrick B., Christman B., Berry, Jr L. C. and King G. Expression of a Procaryotic Gene in Cultured Lung Endothelial Cells after Lipofection with a Plasmid Vector. *Am. J. Respir. Cell Mol. Biol.* 1: 95–100 (1989).

Demeneix B. A., Fredriksson G., Lezoual'ch F., Daugeras-Bernard N., Behr J. P. and Loeffler J. P., Gene Transfer into Intact Vertebrate Embryos. *Int. J. Dev. Biol.* 35; 481–484 (1991).

Düzgünes N., Goldstein J. A., Friend D. S. and Felgner P. L., Fusion of Liposomes Containing a Novel Cationic Lipid, N-[2,3-(Dioleyloxy)propyl]-N,N,N-trimethylammonium: Induction by Multivalent Anions and Asymmetric Fusion with Acidic Phospholipid Vesicles. *Biochemistry* 28: 9179–9184 (1989).

Fasbender A. J., Zabner J. and Welsh M. J., Optimization of Cationic Lipid-Mediated Gene Transfer to Airway Epithelia. *Am. J. Physiol.* 269: 45–51 (1995).

Felgner P. L., Gadek T. R., Holm M., Roman R., Chan H. W., Wenz M., Northrop J. P., Ringold G. and Danielsen M., Lipofection: A Highly Efficient Lipid-Mediated DNA-Transfection Procedure. *Proc. Natl. Acad. Sci. USA* 84: 7413–7417 (1987).

Gao X. and Huang L., A Novel Cationic Liposome Reagent for Efficient Transfection of Mammalian Cells. *Biochem. Biophys. Res. Com.* 179: 280–285 (1991).

Guershon H., Ghirlando R., Guttman S. B. and Minsky A., Mode of Formation and Structural Features of DNA-Cationic Liposome Complexes Used for Transfection. *Biochemistry* 32: 7143–7151 (1993).

Gustafsson J., Arvidson G., Karlsson G. and Almgren M. Complexes between Cationic Liposomes and DNA Visualized by Cryo-TEM. *Biochim. Biophys. Acta* 1235: 305–312 (1995).

Hui S. W., Langner M., Zhao Y. L., Ross P., Hurley E. and Chan K., The role of Helper Lipid Cationic Liposome-Mediated Gene Transfer. *Biophys. J.* 71: 590–599 (1996).

Hofland H. E. J., Shephard L. and Sullivan S. M., Formation of Stable Cationic Lipid/DNA Complexes for Gene Transfer. *Proc. Natl. Acad. SCI. USA* 93: 7305–7309 (1996).

Pinnaduwage P., Schmitt L. and Huang L., Use of a Quaternary Ammonium Detergent in Liposome Mediated DNA Transfection of Mouse L-Cells. *Biochim. Biophys. Acta* 985: 33–37 (1989).

Sternberg B., Sorgi F. L. and Huang L., New Structures in Complex Formation between DNA and Cationic Liposomes Visualized by Freeze-Fracture Electron Microscopy. *FEBS Lett.* 356: 361–366 (1994).

Xu Y. and Szoka, Jr F. C., Mechanism of DNA Release from Cationic Liposome/DNA Complexes Used in Cell Transfection. *Biochemistry* 35: 5616–5623 (1996).

What is claimed is:

1. A process for preparing a composition for the transfer of nucleic acids comprising contacting a nucleic acid with a cationic lipid, wherein prior to the contacting step the cationic lipid is heated until a micellar solution is formed.

2. The process according to claim 1, wherein the cationic lipid is heated to a temperature greater than its phase transition temperature.

3. The process according to claim 1, further comprising between the heating step and the contacting step, a step of pre-compaction maturation of the cationic lipid by cooling, modification of the ionic strength and/or modification of the pH of the solution.

4. The process according to claim 1, further comprising, after the contacting step, a step of post-compaction maturation by cooling, modification of the ionic strength and/or modification of the pH of the solution.

5. The process according to claim 1, wherein the contacting is at a pH of between 4 and 10.

6. The process according to claim 5, wherein the pH is between 6 and 9.

7. The process according to claim 1, wherein the contacting is at an ionic strength of between 0 and 2 M.

8. The process according to claim 7, wherein the ionic strength is between 0.01 and 0.5 M.

9. The process according to claim 8, wherein the ionic strength is between 0.05 and 0.2 M.

10. The process according to claim 3, wherein the pre-compaction maturation is by incubating at room temperature.

11. The process according to claim 10, wherein the pre-compaction maturation is by incubating at room temperature for a period of between 0.5 hour and 1 month.

12. The process according to claim 3, wherein the pre-compaction maturation is carried out until organized vermicular, tubular, lamellar, hexagonal and/or columnar aggregates are formed.

13. The process according to claim 12, wherein the pre-compaction maturation is carried out until organized vermicular and/or tubular aggregates appear.

14. The process according to claim 4, wherein the cooling is by incubating at room temperature.

15. The process according to claim 4, wherein the post-compaction maturation is carried out until organized hexagonal, lamellar and/or columnar aggregates are formed.

16. The process according to claim 1, wherein the cationic lipid is a lipopolyamine.

17. The process according to claim 16, wherein the cationic lipid is a lipospermine or a lipothermine.

18. The process according to claim 1, wherein the nucleic acid is a DNA.

19. The process according to claim 18, wherein the DNA is a plasmid, vector or linear fragment.

20. The process according to claim 1, wherein the nucleic acid is an RNA.

21. The process according to claim 1, wherein the cationic lipid comprises lipid adjuvants.

22. The composition prepared by the process of claim 1, wherein the composition has a transfection efficiency in the presence of serum that is about equal to the transfection efficiency in the absence of serum.

23. The composition of claim 22, further comprising one or more lipid adjuvants.

24. A process for the transfer of nucleic acid into cells in vitro or ex vivo comprising contacting the nucleic acid with a previously heated cationic lipid suspension thereby forming a nucleolipid complex, and incubating the cells with the nucleolipid complex.

25. The process according to claim 24, wherein prior to the contacting step the cationic lipid suspension is matured by cooling, modification of the ionic strength and/or modification of the pH.

26. The process according to claim 24, wherein the nucleolipid complex is matured prior to incubation with the cells by cooling, modification of the ionic strength and/or modification of the pH.

* * * * *